United States Patent
Birkel et al.

(10) Patent No.: US 6,716,455 B2
(45) Date of Patent: Apr. 6, 2004

(54) HAIR TREATMENT GELS CONTAINING ITACONIC ACID MONOESTER/ACRYLATE COPOLYMER

(75) Inventors: Susanne Birkel, Darmstadt (DE); Harald Wendel, Ober-Ramstadt (DE); Michael Franzke, Rossdorf (DE); Silke Niesig, Gross-Bieberau (DE)

(73) Assignee: Wella Aktiengesellschaft, Darmstadt (DE)

( * ) Notice: Subject to any disclaimer, the term of this patent is extended or adjusted under 35 U.S.C. 154(b) by 0 days.

(21) Appl. No.: 10/228,408

(22) Filed: Aug. 27, 2002

(65) Prior Publication Data

US 2003/0049224 A1 Mar. 13, 2003

(30) Foreign Application Priority Data

Aug. 31, 2001 (DE) .......................................... 101 42 476

(51) Int. Cl.$^7$ .............................. A61K 9/10; A61K 7/11
(52) U.S. Cl. ................. 424/487; 424/70.16; 424/78.18; 514/844; 514/944
(58) Field of Search .............................. 424/70.16, 487, 424/78.18; 514/844, 944

(56) References Cited

U.S. PATENT DOCUMENTS 5,972,356 A  10/1999  Peffly
6,447,803 B1 *  9/2002  Sorrentino et al. ......... 424/487
2002/0042448 A1  4/2002  Sorrentino et al.

FOREIGN PATENT DOCUMENTS

| DE | 198 16 662 A1 | 10/1999 |
| WO | 99/37278 | 7/1999 |
| WO | 99/39688 | 8/1999 |
| WO | 02/00177 A2 | 1/2002 |

OTHER PUBLICATIONS

National Starch & Chemical Personal Care: "Modify Rheology . . . " Online XP002209084, 0808/2002, pp. 1–13.
Patent Abstract of Japan vol. 1998, No. 11, Sep. 30, 1998 & JP 10 158129 A, Jun. 16, 1998.

* cited by examiner

Primary Examiner—Robert W. Ramsuez
Assistant Examiner—Ebenezer Sackey
(74) Attorney, Agent, or Firm—Michael J. Striker

(57) ABSTRACT

The aqueous hair fixing gel has special rheological properties so that it can be dispensed from a container without dripping or becoming stringy. It contains from 1.5 to 10 percent by weight of at least one itaconic acid monoester/acrylate copolymer and from 0.1 to 15 percent by weight of at least one non-ionic, anionic, zwitterionic or amphoteric hair-fixing polymer. The itaconic acid monoester has a formula $CH_2=C(COOR^1)CH_2COOR^2$, wherein one of $R^1$ and $R^2$ represents hydrogen and the other represents $-(CH_2CH_2O)_x-R^3$, x is between 1 to 100 and $R^3$ is an alkyl group having 8 to 30 carbon atoms. The aqueous hair treatment gel has a pH of greater than 7 and a viscosity of preferably from 2000 to 50,000 mPa.s, as measured at 25° C. The gel is formulated so that there is a gel viscosity maximum as a function of shear rate with increasing shear rate, preferably between 0.1 to 5.0 s$^{-1}$.

18 Claims, 1 Drawing Sheet

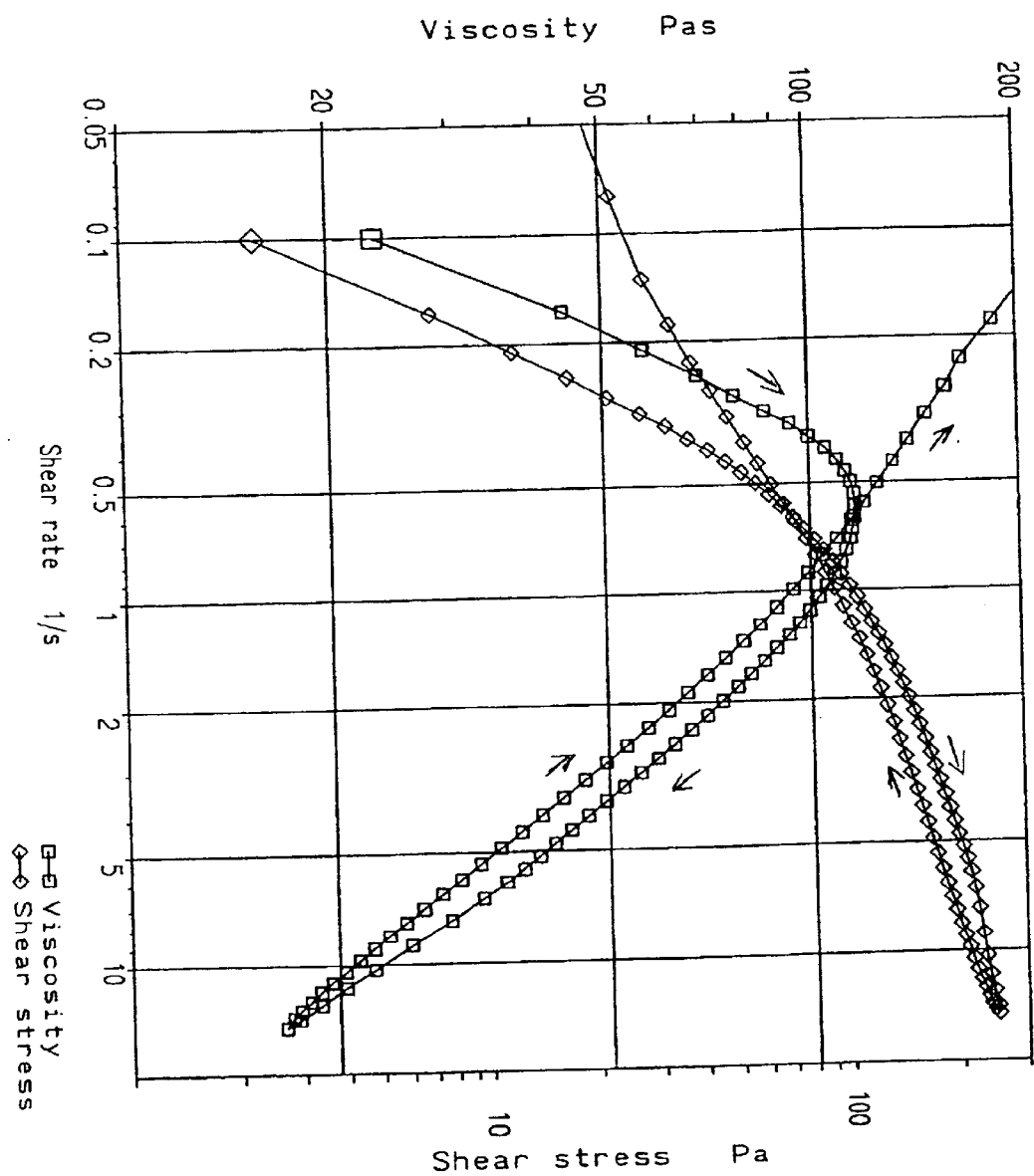

HAIR TREATMENT GELS CONTAINING ITACONIC ACID MONOESTER/ACRYLATE COPOLYMER

BACKGROUND OF THE INVENTION

The subject matter of the invention is a hair treatment composition in gel form, which has special predetermined rheological properties and contains a combination of an itaconic acid monoester/acrylate copolymer and a hair-fixing film-forming polymer.

Hair gels are used for holding and fixing human hair. Conventional hair gels usually contain a combination of gel formers and hair-fixing polymers. The cosmetic hair-fixing polymers usually used for this purpose are characterized by good fixing properties, which more or less satisfactorily hold and fix the hair in a predetermined shape, in aqueous, alcoholic or aqueous-alcoholic media. Frequently however the hair is provided with an only unsatisfactory luster by application of these hair-fixing polymers. Of course a series of additives are known, which are in a position to improve the hair luster, e.g. hydrophobic materials, such as liquid paraffins, isoparaffins, silicone oils or hydrophilic materials, such as multivalent alcohols, especially glycerol or polypropylene glycol. These known, luster-improving materials frequently disadvantageously influence other desired properties of the hair gel. They can act as softeners for the fixing polymer used and thus reduce its fixing power. They can impair the clarity and transparency of the gel, the rheological properties and correspondingly the application properties. Alternatively they still do not provide sufficient hair luster.

An additional important property of hair gel is its rheological behavior. Gels, on the one hand, have high viscosity, and, on the other hand, have the properties of non-Newtonian liquids, especially the properties of pseudo-plastic liquids with or without a flow limit. The viscosity decreases with increasing shear rate (shear thinning). The flow curve is non-linear, i.e. the ratio of the shear stress or shearing force to the shear rate is not constant. This is observable in practice because a gel with these properties has a comparatively high viscosity in the resting phase and/or plastic behavior, but flows readily on application of a comparatively small force and thus is easily removed from its container and easily distributed over the hair. Typically and frequently used gel formers, which form gels having a viscosity that decreases under pressure, are neutralized carbomers (polyacrylic acid).

The viscosity decrease of conventional hair gels caused by shear stress due to their own weight is a disadvantage of these conventional hair gels. Because of that decrease the hair gels can flow. Then the composition can drip from an opened tube containing it, even without an externally applied pressure. Also it can run off vertical or inclined skin or hair surfaces after manual application and, in the case of a gel with thixotropic behavior, even with an increased speed. Undesired dripping or run off of course can be naturally avoided by increasing the base viscosity. However at the same time the application properties, e.g. the distributability and workability of the composition into the hair, are impaired and greater amounts of gel formers are required, which can lead to increased product costs and to increased load on the hair.

SUMMARY OF THE INVENTION

It is an object of the present invention to provide a hair treatment gel of the above-described type, which avoids the disadvantages of the prior art hair treatment gels.

It is a further object of the present invention to provide a hair treatment gel, which provides good hair fixing but at the same time optimizes hair luster, avoids the rheological disadvantages of conventional hair gels and has more attractive, more pleasing haptic properties.

It has now been found that these objects can be attained with a hair treatment gel on an aqueous basis, which has a viscosity of at least 1000 mPa.s at 25° C., a pH of greater than 7 and which contains the following combination of ingredients:

(A) at least 0.5 percent by weight of at least one copolymer of a first monomer and a second monomer, wherein the first monomer is an itaconic acid monoester of the formula $CH_2=C(COOR^1)CH_2COOR^2$, wherein one of $R^1$ and $R^2$ represents hydrogen and the other of $R^1$ and $R^2$ represents the group $-(CH_2CH_2O)_x-R^3$, x is a number between 1 to 100 and $R^3$ is an alkyl group with 8 to 30 carbon atoms, and the second monomer is an acrylate monomer; and (B) at least one non-ionic, anionic, zwitterionic or amphoteric hair-fixing polymer;

but which does not contain a combination of an acrylate/Ceteth-20-itaconate copolymer, cellulose acetate phthalate and $HO-(CH_2CH_2O)_{75}-(CH(CH_3)CH_2O)_{30}-(CH_2CH_2O)_{75}-H$.

The copolymer (A) is preferably present in an amount of from 0.5 to 20, preferably from 1.5 to 10, percent by weight and the hair-fixing polymer (B) is present preferably in an amount of 0.1 to 15, preferably from 0.5 to 10, percent by weight. The hair gel according to the invention is preferably essentially free of cationic polymers, i.e. it contains either no cationic polymers or less than 0.02 percent by weight of cationic polymers. The hair gel according to the invention provides good hair fixing and an improved hair luster at the same time as improved flow properties and an especially pleasant appearance.

It has now been found that these objects may also be attained with a hair treatment gel on an aqueous basis, which has a viscosity of at least 1000 mPa.s at 25° C., a pH of greater than 7 and which contains the following combination of ingredients:

(a) an acrylate/Ceteth-20-itaconate copolymer, (b) cellulose acetate phthalate, and (c) $HO-(CH_2CH_2O)_{75}-(CH(CH_3)CH_2O)_{30}-(CH_2CH_2O)_{75}-H$.

The term "alkyl" in the present disclosure means "monovalent hydrocarbon groups", which can be linear, branched or cyclic.

Copolymer (A)

The copolymer (A) is built up from itaconic acid monoesters of the general formula $CH_2=C(COOR^1)CH_2COOR^2$, wherein one of $R^1$ and $R^2$ represents hydrogen and the other of $R^1$ and $R^2$ represents the group $-(CH_2CH_2O)_x-R^3$, x is a number between 1 to 100, preferably from 10 to 40, especially preferably 20. $R^3$ is an alkyl group with 8 to 30, preferably 12 to 20, carbon atoms, especially cetyl or stearyl are preferred.

The acrylate monomers of the copolymer (A) are preferably selected from the group consisting of acrylic acid, methacrylic acid and their esters, especially the acrylic acid alkyl esters and methacrylic acid alkyl esters with one to ten, especially 1 to 4, carbon atoms in the alkyl group. Suitable copolymers are, for example, acrylic acid or methacrylic acid/itaconic acid polyethoxyalkyl ester copolymers (INCI name:acrylates/Steareth-20 itaconate copolymer and acrylates/Ceteth-20 itaconate copolymer), such as marketed by the firm National Starch, U.S.A. under the trademark Structure® 2001 and Structure® 3001. The acid groups in the polymers used are preferably neutralized by organic or inorganic bases to the extent of 50 to 100%. Suitable neutralization agents are primary or secondary amines, especially aminoalkanols with preferably from 1 to 10 carbon atoms and 1 to 3 hydroxy groups, such as e.g. aminomethyl propanol (AMP), triethanol amine, tetrahydroxypropylethylenediamine or monoethanolamine, but also ammonia, sodium hydroxide, potassium hydroxide, among others.

Hair-Fixing Polymer (B)

The hair-fixing polymer (B) can be non-ionic, anionic, zwitterionic or amphoteric, however preferably anionic or nonionic. It can be a synthetic or natural polymer. The term "natural polymer" means any polymer of natural origin or any polymer of natural origin that has been chemically modified. Those polymers are particularly preferred, which have sufficient solubility in water, alcohol or alcohol/water mixtures, in order to be present in completely dissolved form in the compositions according to the invention. "Hair-fixing polymers" are understood to be those polymers, which, when used in an amount of from 0.01 to 5% in an aqueous, alcoholic or aqueous-alcoholic solution or dispersion, are in a position to deposit a polymer film on the hair and to fix the hair.

Suitable synthetic non-ionic polymers include homopolymers or copolymers, which are built up from at least one of the following monomers:

vinylpyrrolidone, vinylcaprolactam, vinyl esters, such as vinyl acetate, vinyl alcohol, acrylamide, methacrylamide, alkyl- and dialkylacrylamide, alkyl- and dialkylmethacrylamide, dialkylaminoalkylmethacrylamide, dialkylaminoalkylacrylamide, alkylacrylate, alkylmethacrylate, propylene glycol or ethylene glycol, wherein the alkyl groups in these monomers preferably have from one to seven carbon atoms, especially preferably from one to three carbon atoms. For example, homopolymers of vinyl caprolactam, of vinyl pyrrolidone or of N-vinylformamide, are especially suitable. Additional suitable synthetic non-ionic film-forming hair-fixing polymers are, e.g., copolymerizates of vinyl pyrrolidone and vinyl acetate, terpolymers of vinyl pyrrolidone, vinyl acetate and vinyl propionate, terpolymers of vinyl pyrrolidone, vinyl caprolactam and dialkylaminoalkyl(meth)acrylate, terpolymers of vinyl pyrrolidone, vinyl caprolactam and dialkylaminoalkyl (meth)acrylamide, polyacrylamide, polyvinyl alcohols, and hair-fixing polyethylene glycol/polypropylene glycol copolymers. Polyvinylpyrrolidone and polyvinylpyrrolidone/vinyl acetate copolymers are especially preferred.

Suitable anionic hair-fixing polymers include natural or synthetic homo- or copolymers with monomer units containing acid groups, which are copolymerizable with comonomers, if necessary, which contain no acid groups. The acid groups preferably include —COOH, —SO$_3$H, —OSO$_3$H, —OPO$_2$H and —OPO$_3$H groups, of which the carboxylic acid groups are especially preferred. The acid groups of these anionic polymers can be present in partially or completely neutralized form. They are present in the composition according to the invention in a form that is 50% neutralized or in a completely neutralized form. The above-mentioned neutralizing agents may be used to neutralize the acid groups. Suitable monomers include unsaturated, radically polymerizable compounds, which have at least one acid group, especially carboxyvinyl monomers. Suitable monomers containing acid groups include, e.g., acrylic acid, methacrylic acid, crotonic acid, maleic acid and/or maleic acid anhydride or their monoesters, aldehydocarboxylic acids or ketocarboxylic acids.

Comonomers not substituted with acid groups include, e.g., acryl amide, methacrylamides, alkyl and dialkylacrylamides, alkyl and dialkylmethacrylamides, alkylacrylates, alkylmethacrylates, vinyl caprolactone, vinyl pyrrolidone, vinyl esters, vinyl alcohol, propylene glycol or ethylene glycol, amine-substituted vinyl monomers, such as dialkylaminoalkylacrylates, dialkylaminoalkylmethacrylates, monoalkylaminoalkylacrylates and monoalkylaminoalkylmethacrylates, in which the alkyl groups of these monomers preferably contain one to seven carbon atoms, especially preferably from one to three carbon atoms.

Suitable anionic polymers especially include copolymers of acrylic acid or methacrylic acid with monomers selected from the group consisting of acrylic acid esters, methacrylic acid esters, acryl amides, methacrylamides and vinylpyrrolidones, homopolymers of crotonic acid and copolymers of crotonic acid with monomers selected from the group consisting of vinyl esters, acrylic acid esters, methacrylic acid esters, acrylamides and methacrylamides. A suitable natural polymer is, for example, shellac.

Preferred anionic polymers include cross-linked or uncross-linked vinyl acetate/crotonic acid copolymers. Similarly partially esterified copolymers between vinyl methyl ether and maleic acid anhydride are also preferred. Additional suitable anionic polymers include, e.g., terpolymers of acrylic acid, alkyl acrylate and N-alkylacrylamide, especially acrylic acid/ethyl acrylate/N-t-butylacrylamide terpolymer, terpolymers of vinyl acetate, crotonate and vinyl alkanoate, especially vinyl acetate/crotonate/vinyl neodecanoate copolymers.

Suitable film-forming amphoteric polymers include those polymers, which contain both basic or cationic groups, especially primary, secondary and tertiary amine groups, besides acidic or anionic groups, as additional functional groups. For example, suitable amphoteric polymers are copolymers made from alkylacrylamides (especially octylacrylamide), alkylaminoalkylmethacrylates (especially t-butylamino-ethylmethacrylate), and two or more monomers selected from the group consisting of acrylic acid, methacrylic acid and their esters, in which the alkyl groups have from one to four carbon atoms and at least one of the monomers has an acid group, such as those which are obtainable under the trademarks AMPHOMER® and AMPHOMER® LV-71 of National Starch, U.S.A.

Further examples of suitable copolymers include copolymers of acrylic acid, methacrylate and methacrylamideopropyltrimethylammonium chloride (INCI: polyquaternium-47), copolymers made from acrylamidopropyltrimethyl ammonium chloride and acrylates or copolymers made from acrylamide, acrylamidopropyltrimethylammonium chloride, 2-amidopropylacrylamide sulfonate and dimethylaminopropylamine (INCI: Polyquaternium-43). Suitable polymers made with monomers carrying betaine groups, such as copolymers of methacryloylethylbetaine and two or more monomers made from acrylic acid or their simple esters, known under the INCI designation methacryloyl ethyl betaine/acrylates copolymer.

The composition according to the invention is preferably provided in an aqueous, alcoholic or an aqueous-alcoholic medium with preferably at least 10 percent by weight water and preferably up to a maximum amount of 40 percent by weight alcohol. Lower univalent or multivalent alcohols suitable for cosmetic purposes and having from one to four carbon atoms, such as ethanol and isopropanol, may be used as the alcohol. The composition according to the invention has a pH of greater than 7, preferably at least 7.3. At lower pH values the neutralization of the acid groups of the itaconic acid monoester copolymers (A) is insufficient and the consistency is too thin. Values of pH between 7.5 and 8.5 are particularly preferred. In a preferred embodiment the gel contains multivalent alcohols for further improvements in luster, preferably those with 2 to 5 carbon atoms and with 2 to 5 hydroxy groups in an amount of 0.1 to 15 percent by weight, preferably from 1 to 10 percent by weight. Glycerol, ethylene glycol and propylene glycol, especially 1,2-propylene glycol, are especially preferred.

Rheological Properties

The composition of the invention is characterized by a particularly advantageous, special rheological behavior, whereby both the application properties and the haptic properties are improved. A portion of the gel may be dispensed "dry" from its container by pulling off or tearing off, without dripping or becoming stringy. Unintended run off from a containing tube or on inclined surfaces, such as the hand and hair is minimized. Physically the gel according to the invention is characterized by the occurrence of a maximum in the viscosity curve with increasing shear rate. The maximum is typically at shear rates in the vicinity of 0.1 to 5.0, preferably from 0.15 to 2.0, $s^{-1}$, at a temperature of 25° C. During shear stress the flow curve has a turning point where the viscosity attains a maximum value. Another special characteristic is that the viscosity curve for increasing shear rate intersects the curve for decreasing shear rate. The crossing point typically is approximately at a shear rate in the vicinity of 0.05 to 3, preferably 0.1 to 2, $s^{-1}$. At high shear rate the forward curve lies above the back curve and the gel is thixotropic. At low shear rate the forward curve lies under the back curve and the gel is anti-thixotropic. The viscosity and flow curves can be measured, for example with a Bohlin CS System Rheometer, in which the shear rate increases with a linear speed of from 0 to a maximum value, e.g., of about 100 $s^{-1}$, and subsequently is lowered again to the null point, under isothermal conditions (25° C.).

The sole FIGURE shows a typical example of a measurement diagram taken with a Bohlin CS System Rheometer at temperature of 25° C. for a gel according to example 2. The viscosity (viscosity on left axis, measured values shown as square symbols) and shear stress (shear stress on right axis, measured values shown with rhombus symbols) are plotted versus shear rate (X-axis). The arrows next to the curves show the direction of the change of the shear rate. With a shear rate of about 0.6 $s^{-1}$ the viscosity curve has a maximum and the flow curve (shear stress) has a turning point. The forward and the back curves have an intersection at about 0.7 $s^{-1}$.

The viscosity of the gel preferably amounts to from 1000 to 100,000 mPa.s, especially preferably from 2000 to 50,000 mPa.s, and most preferably from 2,500 to 15,000 mPa.s, measured as dynamic viscosity with a Haake VT-550 Rheometer, measurement body SV-DIN at a temperature of 25° C. and a shear rate of 50 $s^{-1}$.

The compositions according to the invention can also contain conventional additive ingredients suitable for hair treatment compositions. These additive ingredients include, e.g. wetting agents or emulsifiers, from the classes of nonionic, anionic, cationic or amphoteric surfactants, such as fatty alcohol sulfates, alkyl benzene sulfonates, alkyltrimethylammonium salts, alkyl betaines, in an amount of from 0.1 to 15 percent by weight; moisturizers; perfume oils in an amount of 0.1 to 1.0 percent by weight; turbidity-imparting agents, such as ethylene glycol distearate, in an amount of about 0.2 to 5.0 percent by weight; pearlescence-imparting agents, such as a mixture of fatty acid monoalkylolamide and ethylene glycol distearate, in an amount of from about 1.0 to 10 percent by weight; bactericidal and fungicidal agents, for example, 2,4,4 trichloro-2-hydroxydiphenyl ether or methyl chloroisothiazolone, in an amount of from 0.01 to 1.0 percent by weight; thickeners, such as coconut fatty acid diethanol amides, in an amount of about 0.2 to 3.0 percent by weight; buffer substances, such as sodium citrate or sodium phosphate, in an amount of from 0.1 to 1.0 percent by weight; colorants, for example, fluorescein sodium salt, in an amount of about 0.1 to 1.0 percent by weight; care materials, such as plant and vegetable extracts, protein and silk hydrolyzates, lanolin derivative compounds, in an amount of 0.1 to 5 percent by weight; physiologically compatible silicone derivative compounds, such as volatile or non-volatile silicone oils or high-molecular-weight siloxane polymers, in an amount of from 0.05 to 20 percent by weight; light protective materials, antioxidants, radical trapping agents, anti-flaking active ingredients, in an amount of about 0.01 to 4 percent by weight; fatty alcohols; luster-imparting agents; vitamins; softening agents; combability-improving agents, de-fatting agents and anti-foaming agents.

The composition according to the invention is preferably in the form of a clear, transparent or at least translucent gel. The gel can be colored or colorless.

The composition according to the invention is characterized by rheological properties, which particularly manifest themselves in an attractive appearance and pleasant haptic properties. The composition may be easily packaged in a tube, a pan or a can and can be dispensed from these containers without leaving a residue, in contrast to currently known commercially available gels packaged in tubes. A portion of the gel according to the invention may pulled off, broken off or separated, without dripping or after-running. The composition is easily distributed on the hair. When formulated as a hair treatment agent it does not load the hair and is especially good for fine hair. It provides a sufficient hold for the hairstyle, without adhering to the hair or loading it. Fine hair becomes full and voluminous. As a hair fixing gel the hair treatment composition provides improved fixing properties and especially a clearly better luster than commercial gels formulated on a carbomer basis.

In a special embodiment the gel according to the invention is suitable for simultaneously fixing and temporarily coloring hair. It contains additionally at least one temporary hair dye pigment. A "temporary hair coloring" means a color change of human hair, which lasts until the next hair washing and which can be removed again by washing the with conventional shampoos. The pigments are, preferably, contained in the composition in an amount of from 0.01 to 25 percent by weight, especially preferably in an amount of 5 to 15 percent by weight. The pigments are preferably micro-pigments, not nano-pigments. The preferred particle size amounts to from 1 to 200 µm, especially from 3 to 150 µm, especially preferably from 10 to 100 µm.

The pigments are practically insoluble coloring agents and can be inorganic or organic. Also inorganic-organic mixed pigments may be used. Inorganic pigments are preferable. The advantage of the inorganic pigments is their outstanding light-resistance, weather-resistance and temperature-resistance. The inorganic pigments can be of natural origin, for example chalk, ocher, umber, green earth, burnt siena or graphite. The pigments can be white pigments, such as titanium dioxide or zinc oxide; black pigments, such as iron oxide black; fancy or multi-colored pigments, such as ultramarine or iron oxide red; lustrous pigments, metal effect pigments, pearlescent pigments as well as fluorescene or phosphorescent pigments. Preferably at least one pigment is a colored, non-white pigment. Metal oxides, metal hydroxides and metal oxide hydrates, mixed phase pigments, sulfur-containing silicates, metal sulfides, complex metallo-cyanides, metal sulfates, metal chromates and metal molybdates and metals themselves (bronze pigments) are suitable. In particular, titanium dioxide (C.I. 77891), black iron oxide (C.I. 77499), yellow iron oxide (C.I. 77492), red and brown iron oxide (C.I. 77491), manganese violet (C.I. 77742), ultramarine (sodium aluminum sulfosilicate, C.I. 77007, Pigment Blue 29), chromium oxide hydrate (C.I. 77289), Iron Blue (Ferric ferrocyanide, C.I. 77510) and carmine (cochineal), are all suitable pigments.

Pigments based on mica and/or isinglass, which are coated with a metal oxide or metal oxychloride, such as titanium dioxide or bismuth oxychloride and if necessary other color-imparting materials, such as iron oxides, iron blue, ultramarine, carmine, etc, whose colors can be modified by changing the thickness of the coating, are especially preferred. Pigments of this sort are marketed, for example, under the trademark, Rona®, Colorona®, Dichrona® and Timiron® by the firm, Merck, Germany.

Organic pigments are, for example, the natural pigments, Sepia, gamboge, charcoal, Kasseler brown, indigo, chlorophyl and other plant pigments. Synthetic organic pigments include, for example, azo pigments, anthrquinoid pigments, indigoid pigments, dioxazine, quinacridone, phthalocyanine isoindolinone pigments, perylene pigments, perinone pigments, metal complex pigments, alkali blue pigments and diketopyrrolopyrrole pigments.

BRIEF DESCRIPTION OF THE DRAWING

The objects, features and advantages of the invention are explained in this description with the aid of the following sole FIGURE, which is graphical illustration showing the rheological behavior of a hair treatment gel according to the invention, particularly the dependence of viscosity and shear stress on shear rate.

EXAMPLES

The following examples should clearly illustrate the subject matter of the invention. The polymer content given in the examples is based on the solid content.

Example 1

Hair Gel

|  | A | B |
|---|---|---|
| PVA/VA Copolymer | 8.0 g | 8.0 g |
| Acrylates/Ceteth-20 Itaconate copolymer | 3.0 g | — |
| Carbomer | — | 0.5 g |
| Propylene glycol | 2.7 g | 2.7 g |

-continued

|  | A | B |
|---|---|---|
| Aminomethylpropanol | 1.425 g | 0.5 g |
| Water | to 100 g | To 100 g |

Two hair gels of comparable viscosity were prepared and compared in regard to their hair luster and hair fixing power. Gel A is according to the invention and gel B is a commercial gel on the basis of carbomer. For luster measurement 0.5 g portions of gel were applied to respective 2 g hair strand samples. The strand samples were dried over night at 65 percent relative humidity and at 20° C. The luster measurement took place by directing a parallel light beam to a test surface and measuring the angular distribution of the reflected light and of the light scattered in or under the surface. The higher the amount of directly reflected light and the less the amount of scattered light, the higher the luster. A luster classification can occur by measurement and evaluation of the angular distribution of the light returned from the test surface. A small angular distribution (smaller half-width, HWB) means a greater luster and a broad angular distribution (larger half-width, HWB) means a poorer luster. The measurement of the angular distribution occurs with a digital camera, the data are read into a computer and evaluated with image processing software (Optimate 5.2). Six measurements were performed per sample and the average values were formed.

| Untreated Strands: | HWB = 40° |
|---|---|
| Sample A: | HWB = 35° |
| Sample B: | HWB = 37° |

The change of thickeners leads surprisingly to an increase of hair luster. The measurement results correlate with a visual luster evaluation of the strands by a panel of experts experienced in the evaluation of hair quality.

The comparison of the fixing performance occurs by measurement of the curl retention CR. The gel portions were applied to the respective hair strand samples. The strands were wound on spiral curlers after an acting time of 10 minutes, and stored for 30 minutes at 70° C. and for one hour at 20° C. and a relative humidity of 85%. Subsequently the strands were removed from the curlers and loaded with a 50 mg weight and suspended. The lengths of the strand samples were measured after 5 hours and the curl retentions were calculated from the measured lengths by the following formula.

$$CR=(L_0-L_t)/(L_0-L_1)*100\%$$

wherein
 $L_0$=Length of the stretched strand samples;
 $L_t$=Length of the suspended strand samples; and
 $L_1$=Length of the wound strand samples.
Three measurement values were obtained per sample and the results were averaged.

| Untreated strand samples: | CR (5h) = 42%; CR (24h) = 21%; |
|---|---|
| Sample A: | CR (5h) = 75%; CR (24h) = 60%; |
| Sample B: | CR (5h) = 47%; CR (24h) = 29%. |

The change or replacement of the thickener leads to surprisingly higher curl retention in the hair sample treated with gel sample A according to the invention.

Example 2

Hair Gel

| | |
|---|---|
| PVA/VA Copolymer | 1.0 g |
| Acrylates/Ceteth-20 Itaconate copolymer | 3.0 g |
| Aminomethylpropanol | 1.6 g |
| Water | To 100 g |
| Viscosity about 6550 mPa · s (25° C.) | |

The flow and viscosity curves with increasing and decreasing shear rates in the vicinity of 0 to 20 $s^{-1}$ are shown in FIG. 1.

Example 3

Hair Gel

| | |
|---|---|
| PVA/VA Copolymer | 2.0 g |
| Acrylates/Ceteth-20 Itaconate copolymer | 1.5 g |
| Aminomethylpropanol | 0.8 g |
| PEG-40 Hydrogenated Castor Oil | 0.3 g |
| Perfume | 0.2 g |
| Water | To 100 g |
| Viscosity about 2600 mPa · s (25° C.) | |

Example 4

Hair Gel

| | |
|---|---|
| VA/Crotonates Copolymer(Luviset ® 66) | 1.0 g |
| Acrylates/Ceteth-20 Itaconate copolymer | 2.25 g |
| Aminomethylpropanol | 1.4 g |
| PEG-40 Hydrogenated Castor Oil | 0.3 g |
| Perfume | 0.2 g |
| Water | To 100 g |
| Viscosity about 5800 mPa · s (25° C.) | |

Example 5

Hair Gel

| | |
|---|---|
| VA/Crotonates Copolymer(Luviset ® 66) | 1.0 g |
| Acrylates/Ceteth-20 Itaconate copolymer | 2.25 g |
| Aminomethylpropanol | 1.4 g |
| Polysorbate 40 | 0.8 g |
| Timiron ® Gold Plus MP-25 | 0.2 g |
| Water | To 100 g |
| Viscosity about 5600 mPa · s (25° C.) | |

Example 6

Hair Gel

| | |
|---|---|
| Octylacrylamide/acrylates/ Butylaminoethyl methacrylate copolymer (Amphomer ®) | 2.5 g |
| Acrylates/Ceteth-20 Itaconate copolymer | 1.5 g |
| Aminomethylpropanol | 1.23 g |
| FD&C Green No. 3 (C.I. 42053) | 0.1 g |
| Water | To 100 g |
| Viscosity about 3600 mPa · s (25° C.) | |

Example 7

Hair Gel

| | |
|---|---|
| Polyvinylpyrrolidone K80 | 2.0 g |
| Acrylates/Ceteth-20 Itaconate copolymer | 3.75 g |
| Aminomethylpropanol | 2.0 g |
| Polysorbate 40 | 0.8 g |
| Perfume | 0.1 g |
| Water | To 100 g |
| Viscosity about 14200 mPa · s (25° C.) | |

The disclosure in German Patent Application 101 42 476.0 of Aug. 31, 2001 is incorporated here by reference. This German Patent Application describes the invention described hereinabove and claimed in the claims appended hereinbelow and provides the basis for a claim of priority for the instant invention under 35 U.S.C. 119.

While the invention has been illustrated and described as embodied in a hair treatment gel containing itaconic acid monoester/acrylate copolymer, it is not intended to be limited to the details shown, since various modifications and changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and is set forth in the following appended claims.

We claim:

1. An aqueous hair treatment gel having a viscosity of at least 1000 mPa.s, as measured at 25° C. and at a shear rate of 50 $s^{-1}$, a pH of greater than 7 and which contains water and at least 0.5 percent by weight of at least one copolymer of a first monomer and a second monomer, said first monomer being an itaconic acid monoester of formula $$CH_2=C(COOR^1)CH_2COOR^2,$$

wherein one of $R^1$ and $R^2$ represents hydrogen and another of $R^1$ and $R^2$ represents $—(CH_2CH_2O)_x—R^3$, x is a number between 1 to 100 and $R^3$ is an alkyl group having 8 to 30 carbon atoms, and said second monomer being an acrylate monomer; and at least one non-ionic, anionic, zwitterionic or amphoteric hair-fixing polymer;

but which does not contain a combination of an acrylate/Ceteth-20-itaconate copolymer, cellulose acetate phthalate and HO—$(CH_2CH_2O)_{75}$—$(CH(CH_3)CH_2O)_{30}$—$(CH_2CH_2O)_{75}$—H;

wherein said viscosity depends on shear rate when said shear rate is increasing so that said viscosity has a maximum viscosity value at a shear rate value between 0.1 and 5.0 s$^{-1}$.

2. The aqueous hair treatment gel as defined in claim 1, containing from 1.5 to 10 percent by weight of said at least one copolymer of said first monomer and said second monomer.

3. The aqueous hair treatment gel as defined in claim 1, containing from 0.1 to 15 percent by weight of said at least one non-ionic, anionic, zwitterionic or amphoteric hair-fixing polymer.

4. The aqueous hair treatment gel as defined in claim 1, wherein said R$^3$ represents an alkyl group having 12 to 20 carbon atoms and said x represents a number from 10 to 40.

5. The aqueous hair treatment gel as defined in claim 1, wherein said second monomer is selected from the group consisting of acrylic acid, methacrylic acid, acrylic acid alkyl esters and methacrylic acid alkyl esters, and wherein said alkyl esters contain alkyl groups having from 1 to 10 carbon atoms.

6. The aqueous hair treatment gel as defined in claim 1, wherein said at least one non-ionic, anionic, zwitterionic or amphoteric hair-fixing polymer is polyvinylpyrrolidone, vinylpyrrolidone/vinyl acetate copolymer, vinyl acetate/crotonic acid copolymer, a terpolymer of vinyl acetate, crotonate and vinyl alkanoate, a partially esterified copolymer of vinylmethyl ether and maleic acid anhydride, a copolymer of acrylic or methacrylic acid with an alkylacrylate or an N-alkylacrylamide and a polystyrene sulfonate or a copolymer of an alkylacrylamide, alkylaminoalkyl methacrylate and two or more monomeric compounds; wherein said monomeric compounds are each selected from the group consisting of acrylic acid, methacrylic acid, alkyl esters of acrylic acid and alkyl esters of methacrylic acid; and wherein at least one of said monomeric compounds contains an organic acid group and said alkyl esters contain alkyl groups having from one to four carbon atoms.

7. The aqueous hair treatment gel as defined in claim 1, substantially free of cationic polymers.

8. The aqueous hair treatment gel as defined in claim 1, further comprising at least one alcoholic ingredient selected from the group consisting of monovalent alcohols with from 1 to 4 carbon atoms and polyvalent alcohols with from 2 to 5 carbon atoms.

9. An aqueous hair treatment gel having a viscosity of at least 1000 mPa.s, as measured at 25° C. and at a shear rate of 50 s$^{-1}$, a pH of greater than 7 and which contains water and at least 0.5 percent by weight of at least one copolymer of a first monomer and a second monomer, said first monomer being an itaconic acid monoester of formula

wherein one of R$^1$ and R$^2$ represents hydrogen and another of R$^1$ and R$^2$ represents —$(CH_2CH_2O)_x$—R$^3$, x is a number between 1 to 100 and R$^3$ is an alkyl group having 8 to 30 carbon atoms, and said second monomer being an acrylate monomer;

at least one non-ionic, anionic, zwitterionic or amphoteric hair-fixing polymer; and at least one hair-coloring pigment;

wherein said viscosity depends on shear rate when said shear rate is increasing so that said viscosity has a maximum viscosity value at a shear rate value between 0.1 and 5.0 s$^{-1}$.

10. The aqueous hair treatment gel as defined in claim 9, containing from 0.01 to 25 percent by weight of said at least one hair-coloring pigment and wherein said at least one hair-coloring pigment is a metal oxide pigment, ultramarin, a lustrous pigment, a metal effect pigment, a pearlescent pigment, a fluorescene pigment, a phosphorescent pigment, a metal hydroxide pigment, a metal oxide hydrate pigment, a mixed phase pigment, a sulfur-containing silicate pigment, a metal sulfide pigment, a metal cyanide complex pigment, a metal sulfate pigment, a metal chromate pigment, a metal molybdate pigment, a bronze pigment, carmine or a mica-based pigment, and wherein said mica-based pigment is coated with a metal oxide layer or metal oxychloride layer and, optionally, with iron oxide, iron blue, said ultramarine or said carmine, and said layer has a layer thickness according to a predetermined color effect.

11. An aqueous hair treatment gel having a viscosity of from 2000 to 50,000 mPa.s, as measured at 25° C. and at a shear rate of 50 s$^{-1}$, a pH of greater than 7 and which contains water and from 1.5 to 10 percent by weight of at least one copolymer of a first monomer and a second monomer, said first monomer being an itaconic acid monoester of formula

wherein one of R$^1$ and R$^2$ represents hydrogen and another of R$^1$ and R$^2$ represents —$(CH_2CH_2O)_x$—R$^3$, x is a number between 1 to 100 and R$^3$ is an alkyl group having 8 to 30 carbon atoms, and said second monomer being an acrylate monomer; and from 0.1 to 15 percent by weight of at least one non-ionic, anionic, zwitterionic or amphoteric hair-fixing polymer;

wherein said viscosity depends on shear rate when said shear rate is increasing so that said viscosity has a maximum viscosity value at a shear rate value between 0.1 and 5.0 s$^{-1}$.

12. An aqueous hair treatment gel having a viscosity of at least 1000 mPa.s, as measured at 25° C. and at a shear rate of 50 s$^{-1}$, a pH of greater than 7 and which contains water and at least 0.5 percent by weight of at least one copolymer of a first monomer and a second monomer, said first monomer being an itaconic acid monoester of formula

wherein one of R$^1$ and R$^2$ represents hydrogen and another of R$^1$ and R$^2$ represents —$(CH_2CH_2O)_x$—R$^3$, x is a number between 1 to 100 and R$^3$ is an alkyl group having 5 to 30 carbon atoms, and said second monomer being an acrylate monomer; and at least one non-ionic, anionic, zwitterionic or amphoteric hair-fixing polymer, but which does not contain a combination of an acrylate/Ceteth-20-itaconate copolymer, cellulose acetate phthalate and HO—$(CH_2CH_2O)_{75}$—$(CH(CH_3)CH_2O)_{30}$—$(CH_2CH_2O)_{75}$—H;

wherein said at least one non-ionic, anionic, zwitterionic or amphoteric hair-fixing polymer is polyvinylpyrrolidone, vinylpyrrolidone/vinyl acetate copolymer, vinyl acetate/crotonic acid copolymer, a terpolymer of vinyl acetate, crotonate and vinyl alkanoate, a partially esterified copolymer of vinylmethyl ether and maleic acid anhydride, a copolymer of acrylic or methacrylic acid with an alkylacrylate or an N-alkylacrylamide and a polystyrene sulfonate or a copolymer of an alkylacrylamide, alkylaminoalkyl methacrylate and two or more monomeric compounds; wherein said monomeric compounds are each selected from the group consisting of acrylic acid, methacrylic acid, alkyl esters of acrylic acid and alkyl esters of methacrylic acid; and wherein at least one of said monomeric compounds contains an organic acid group and said alkyl esters contain alkyl groups having from one to four carbon atoms.

13. The aqueous hair treatment gel as defined in claim 12, containing from 1.5 to 10 percent by weight of said at least one copolymer of said first monomer and said second monomer and from 0.1 to 15 percent by weight of said at least one non-ionic, anionic, zwitterionic or amphoteric hair-fixing polymer.

14. The aqueous hair treatment gel as defined in claim 1, wherein said second monomer is selected from the group consisting of acrylic acid, methacrylic acid, acrylic acid alkyl esters and methacrylic acid alkyl esters, and wherein said alkyl esters contain alkyl groups having from 1 to 10 carbon atoms.

15. An aqueous hair treatment gel having a viscosity of at least 1000 mPa.s, as measured at 25° C. and at a shear rate of 50 s$^{-1}$, a pH of greater than 7 and which contains water and at least 0.5 percent by weight of at least one copolymer of a first monomer and a second monomer, said first monomer being an itaconic acid monoester of formula

wherein one of $R^1$ and $R^2$ represents hydrogen and another of $R^1$ and $R^2$ represents $—(CH_2CH_2O)_x—R^3$, x is a number between 1 to 100 and $R^3$ is a cetyl group, and said second monomer being an acrylate monomer; and at least one non-ionic, anionic, zwitterionic or amphoteric hair-fixing polymer;

but which does not contain a combination of an acrylate/Ceteth-20-itaconate copolymer, cellulose acetate phthalate and $HO—(CH_2CH_2O)_{75}—(CH(CH_3)CH_2O)_{30}—(CH_2CH_2O)_{75}—H$.

16. The aqueous hair treatment gel as defined in claim 15, wherein said at least one non-ionic, anionic, zwitterionic or amphoteric hair-fixing polymer is polyvinylpyrrolidone, vinylpyrrolidone/vinyl acetate copolymer, vinyl acetate/crotonic acid copolymer, a terpolymer of vinyl acetate, crotonate and vinyl alkanoate, a partially esterified copolymer of vinylmethyl ether and maleic acid anhydride, a copolymer of acrylic or methacrylic acid with an alkylacrylate or an N-alkylacrylamide and a polystyrene sulfonate or a copolymer of an alkylacrylamide, alkylaminoalkyl methacrylate and two or more monomeric compounds; wherein said monomeric compounds are each selected from the group consisting of acrylic acid, methacrylic acid, alkyl esters of acrylic acid and alkyl esters of methacrylic acid; and wherein at least one of said monomeric compounds contains an organic acid group and said alkyl esters contain alkyl groups having from one to four carbon atoms.

17. The aqueous hair treatment gel as defined in claim 15, wherein said second monomer is selected from the group consisting of acrylic acid, methacrylic acid, acrylic acid alkyl esters and methacrylic acid alkyl esters, and wherein said alkyl esters contain alkyl groups having from 1 to 10 carbon atoms.

18. The aqueous hair treatment gel as defined in claim 15, containing from 1.5 to 10 percent by weight of said at least one copolymer of said first monomer and said second monomer and from 0.1 to 15 percent by weight of said at least one non-ionic, anionic, zwitterionic or amphoteric hair-fixing polymer.

* * * * *